(12) United States Patent
Ueda et al.

(10) Patent No.: US 11,992,240 B2
(45) Date of Patent: May 28, 2024

(54) PUNCTURE SYSTEM

(71) Applicant: TERUMO KABUSHIKI KAISHA, Tokyo (JP)

(72) Inventors: Ryosuke Ueda, Shizuoka (JP); Takashi Kumazawa, Shizuoka (JP); Ryosuke Maeda, Shizuoka (JP); Toshiaki Shinohara, Yamanashi (JP); Masaaki Watanabe, Shizuoka (JP); Yuusuke Uchida, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 846 days.

(21) Appl. No.: 17/110,747

(22) Filed: Dec. 3, 2020

(65) Prior Publication Data

US 2021/0085362 A1    Mar. 25, 2021

Related U.S. Application Data

(63) Continuation of application No. PCT/JP2019/022306, filed on Jun. 5, 2019.

(30) Foreign Application Priority Data

Jun. 6, 2018    (JP) ................................ 2018-108638

(51) Int. Cl.
*A61B 17/34* (2006.01)
*A61B 34/32* (2016.01)
(Continued)

(52) U.S. Cl.
CPC .......... *A61B 17/3403* (2013.01); *A61B 34/32* (2016.02); *A61B 2034/303* (2016.02); *A61M 25/0113* (2013.01)

(58) Field of Classification Search
CPC ................ A61B 17/3403; A61B 34/32; A61B 2034/303; A61M 25/0113
See application file for complete search history.

(56) References Cited

U.S. PATENT DOCUMENTS 8,888,714 B1 * 11/2014 Soto .................. A61B 5/15003
600/576
11,510,616 B2 * 11/2022 Kopperschmidt ..... A61B 8/085
(Continued)

FOREIGN PATENT DOCUMENTS

| CN | 101583312 A | 11/2009 |
|---|---|---|
| CN | 104203098 A | 12/2014 |

(Continued)

OTHER PUBLICATIONS

International Search Report (PCT/ISA/210) and translation and Written Opinion (PCT/ISA/237) dated Sep. 3, 2019, by the Japanese Patent Office as the International Searching Authority for International Application No. PCT/JP2019/022306.
(Continued)

*Primary Examiner* — Phong H Dang
(74) *Attorney, Agent, or Firm* — Buchanan Ingersoll & Rooney PC

(57) ABSTRACT

A puncture system that is configured to automatically puncture a radial artery of a hand of a patient includes: a grip to be gripped by the hand; a blood vessel detection unit that detects a position of an artery of the hand that grips the grip; an adjustment mechanism that adjusts a relative posture of the grip and a puncture needle a forward mechanism to move the puncture needle forward toward the grip; and a control unit that determines, in accordance with the position of the artery detected by the blood vessel detection unit, a relative posture of the grip and the puncture needle and a forward distance of the puncture needle, and controls operations of (Continued)

the adjustment mechanism and the forward mechanism on the basis of the posture and the forward distance having been determined.

19 Claims, 13 Drawing Sheets

(51) Int. Cl.
*A61B 34/30* (2016.01)
*A61M 25/01* (2006.01)

(56) References Cited

U.S. PATENT DOCUMENTS

| | | | |
|---|---|---|---|
| 11,844,524 B1* | 12/2023 | Reu | A61B 18/1492 |
| 11,845,723 B2* | 12/2023 | Sawa | A61P 35/00 |
| 2004/0171923 A1* | 9/2004 | Kalafut | A61B 5/0059 |
| | | | 600/407 |
| 2005/0222554 A1 | 10/2005 | Wallace et al. | |
| 2008/0275396 A1* | 11/2008 | Neerken | A61B 5/15003 |
| | | | 604/116 |
| 2010/0030037 A1 | 2/2010 | Matsumoto et al. | |
| 2010/0222703 A1 | 9/2010 | Takashima et al. | |
| 2012/0190981 A1* | 7/2012 | Harris | A61B 5/150946 |
| | | | 604/95.01 |
| 2014/0336535 A1 | 11/2014 | Richter et al. | |
| 2015/0065916 A1* | 3/2015 | Maguire | A61B 5/150748 |
| | | | 600/573 |
| 2015/0374273 A1* | 12/2015 | Maguire | A61M 5/427 |
| | | | 600/573 |
| 2016/0184032 A1 | 6/2016 | Romo et al. | |
| 2017/0035335 A1* | 2/2017 | Breteau | A61B 17/12036 |

FOREIGN PATENT DOCUMENTS

| | | |
|---|---|---|
| CN | 106580344 A | 4/2017 |
| CN | 107049431 A | 8/2017 |
| CN | 108056780 A | 5/2018 |
| JP | 2005095281 A | 4/2005 |
| JP | 2008536612 A | 9/2008 |
| JP | 2013013529 A | 1/2013 |
| JP | 2017506999 A | 3/2017 |
| JP | 2018500054 A | 1/2018 |

OTHER PUBLICATIONS

An English Translation of the International Search Report (Form PCT/ISA/210) and the Written Opinion of the International Searching Authority (Form PCT/ISA/237) dated Sep. 3, 2019, by the Japanese Patent Office in corresponding International Application No. PCT/JP2019/022306. (6 pages).

Office Action (The First Office Action) dated Mar. 14, 2022, by the State Intellectual Property Office of People's Republic of China in corresponding Chinese Patent Application No. 201980037044.2 and an English Translation of the Office Action. (19 pages).

* cited by examiner

PUNCTURE SYSTEM

CROSS-REFERENCES TO RELATED APPLICATIONS

This application is a continuation of International Application No. PCT/JP2019/022306 filed on Jun. 5, 2019, which claims priority to Japanese Patent Application No. 2018-108638 filed on Jun. 6, 2018, the entire content of both of which is incorporated herein by reference.

FIELD OF THE INVENTION

The present invention generally relates to a puncture system and a puncture method.

BACKGROUND DISCUSSION

A therapeutic procedure in which percutaneous diagnosis and treatment are performed by puncturing a blood vessel of a limb such as an arm or a leg by a puncture needle, introducing an introducer sheath into the blood vessel via a puncture site, and delivering a medical appliance such as a catheter to a lesion area via a lumen of the introducer sheath, has been conventionally performed.

In order to perform the puncture independent of the ability of a doctor or the like, JP-T 2008-536612 (the term "JP-T" as used herein means a published Japanese translation of a PCT patent application) discloses a system that automatically punctures a blood vessel. The system disclosed in this patent application publication includes: an acquisition module that acquires a position or the like of a blood vessel; a control unit that can determine a puncture position of the blood vessel depending on output from the acquisition module; an operation unit capable of moving a puncture needle; and the like.

SUMMARY

Meanwhile, in recent years, a catheter therapeutic procedure by distal transradial intervention (dTRI) in which a blood vessel of a hand is punctured, and treatment is performed via the puncture site has been attempted. When the hand is punctured, a posture of a puncture needle needs to be adjusted according to a posture of the hand. However, the system disclosed in JP-T 2008-536612 is not configured to adjust the posture of the puncture needle according to the posture of the hand.

A puncture system disclosed here is configured to automatically puncture a blood vessel of a hand by adjusting a posture of a puncture needle in accordance with a posture of the hand.

A puncture system that is configured to automatically puncture a blood vessel of a hand of a patient, and includes: a grip to be gripped by the hand; a blood vessel detection unit configured to detect a position of the blood vessel of the hand that grips the grip; an adjustment mechanism configured to adjust a relative posture of the grip and a puncture needle; a forward mechanism configured to move the puncture needle forward toward the grip; and a control unit that determines, in accordance with the position of the blood vessel detected by the blood vessel detection unit, a relative posture of the grip and the puncture needle and a forward distance of the puncture needle, and controls operations of the adjustment mechanism and the forward mechanism on the basis of the posture and the forward distance having been determined.

The puncture system is able to automatically puncture a blood vessel of a hand by adjusting a posture of a puncture needle in accordance with a posture of the hand.

In accordance with another aspect, a puncture system is configured to automatically puncture a blood vessel in a hand of a patient with a puncture needle, wherein the patient's hand includes fingers and a thumb. The puncture system comprises: a grip to be gripped by the hand of the patient, the grip including a hole sized to receive the thumb of the patient's hand or at least one of the fingers of the patent's hand; a grip actuator that holds the grip and adjusts a posture of the grip; a puncture needle holder configured to hold the puncture needle and move the puncture needle toward and away from the grip; a puncture needle actuator operatively connected to the puncture needle holder to adjust a posture of the puncture needle; a blood vessel detection unit that detects a position of the blood vessel of the hand of the patient that grips the grip; and a control unit that determines, in accordance with the position of the blood vessel detected by the blood vessel detection unit and a relative posture of the grip and the puncture needle, a forward movement distance to move the puncture needle to puncture the blood vessel in the hand of the patient, and controls operations of the puncture needle holder based on the forward movement distance determined by the control unit.

Another aspect involves a method of automatically puncturing a blood vessel in a hand of a patient with a puncture needle. The method comprises: detecting a position of a blood vessel in a hand of a patient while the hand of the patient is gripping a grip; determining a relative posture of the grip and the puncture needle, and a forward movement distance to move the puncture needle, using the detected position of the blood vessel; changing the posture of the grip and/or the puncture needle so that the relative posture of the grip and the puncture needle is the determined relative posture of the grip and the puncture needle; and moving the puncture needle the forward movement distance to puncture the blood vessel.

DETAILED DESCRIPTION

Set forth below with reference to the accompanying drawings is a detailed description of embodiments of a puncture system representing examples of the inventive puncture system disclosed here. The dimensions or scales on the drawings may be exaggerated or different from actuality/reality for convenience of description and illustration.

FIGS. 1 to 10 are views to be used for an explanation of a puncture system 1 according to an embodiment of the present invention.

Figure 8A:
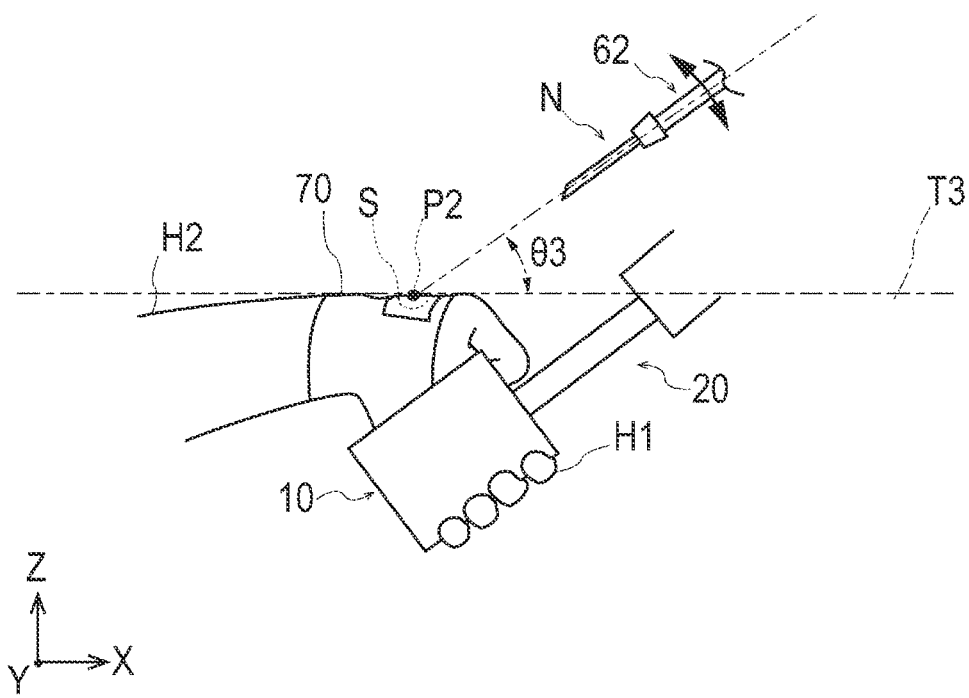
FIG. 8A is a view to be used for an explanation of an operation of the puncture actuator of the puncture system according to the embodiment of the present invention.
Figure 8B:
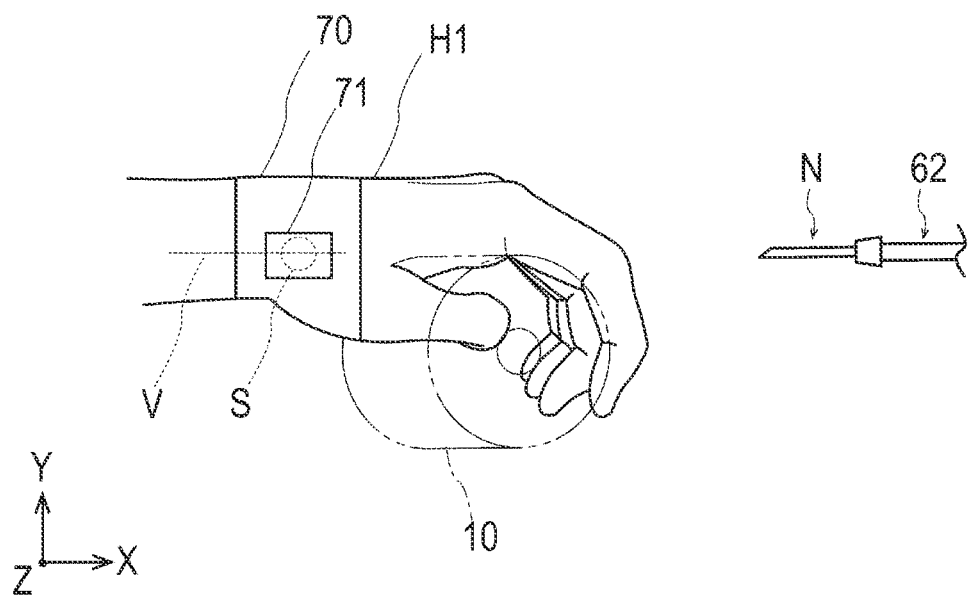
FIG. 8B is a view to be used for an explanation of the operation of the puncture actuator of the puncture system according to the embodiment of the present invention.

The puncture system 1 is configured, as illustrated in FIG. 8B, in the present embodiment, as a system that automatically punctures, in a radial artery V (corresponding to a blood vessel) that extends on a dorsal side of a hand H1 of a patient, the radial artery in a snuff box or a distal radial artery that extends on a side of a fingertip from the snuff box.

Herein, the radial artery in the snuff box is a radial artery (Frank H. Netter, "radial artery in anatomical snuff box", Atlas of Human Anatomy, 4th Edition) in a site that is positioned at a peripheral side of the radial artery and between an extensor pollicis brevis tendon and an extensor pollicis longus tendon, and is referred to an s-RA hereinafter. Moreover, herein, the distal radial artery is a dorsal carpal branch of the radial artery and is a radial artery that is positioned between the extensor pollicis longus tendon and the extensor carpi radialis longus tendon, and is referred to as a d-RA hereinafter. In the following explanation of the embodiment, an example in which the puncture system 1 punctures the s-RA of a left hand of the patient will be described, however, the puncture system 1 may puncture the d-RA. Moreover, the hand H1 that serves as a use target of the puncture system 1 may be a right hand.

Figure 1:
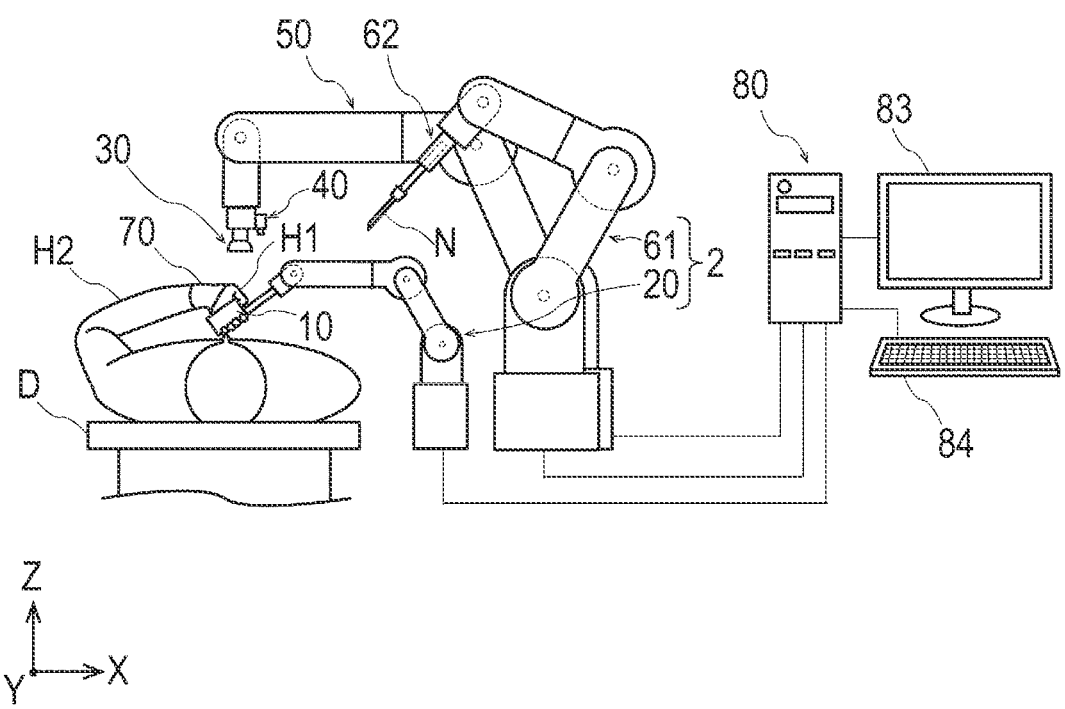
FIG. 1 is a schematic view illustrating a puncture system according to an embodiment of the present invention.

Referring to FIG. 1, the puncture system 1 includes a grip 10, a grip actuator 20, a blood vessel detection unit 30, a reversed blood detection unit 40, a detection actuator 50, a puncture actuator 61, a forward mechanism 62, a restrainer 70, and a control unit 80. In the present embodiment, the grip actuator 20 and the puncture actuator 61 configure an adjustment mechanism 2 that adjusts a relative posture of the grip 10 and a puncture needle N. The following describes the respective units or parts of the puncture system 1 in details.

(Grip)

The grip 10 is gripped, as illustrated in FIG. 1, by the user's (patient's) hand H1. The grip 10 in a state of being gripped by the hand H1 is configured to be capable of being disposed above an abdominal region of a patient who is lying on his/her back on an operating table D.

Figure 2:
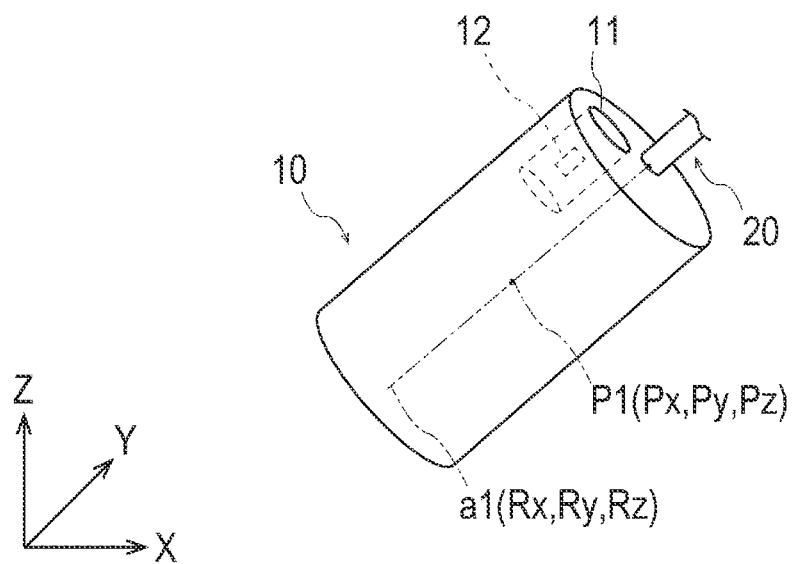
FIG. 2 is a perspective view illustrating a grip of the puncture system according to the embodiment of the present invention.

The grip 10 has, in the present embodiment, as illustrated in FIG. 2, a cylindrical shape that extends in a direction (axis direction or axial direction a1) along which the fingers other than the thumb are arranged. An appearance shape of the grip 10 is not specifically limited as long as it is the shape that the grip 10 extends in the direction along which the fingers other than the thumb are arranged so as to allow the grip 10 to be gripped by the hand H1.

As shown in FIG. 2, a hole portion (e.g., blind hole) 11 is provided in one axial end portion of the grip 10. This hole portion 11 allows the thumb to be inserted. In the hole portion 11, a thumb detection unit 12 capable of detecting that the thumb has been disposed in the hole portion 11 (i.e., that the thumb is disposed in the hole portion 11) is provided. The position of the hole portion 11 is not specifically limited as long as it is the position at which the thumb is capable of being inserted in a state where the fingers other than the thumb are disposed on a side surface (peripheral surface) of the grip 10.

The thumb detection unit 12 is not specifically limited as long as it is capable of detecting that the thumb is disposed in the hole portion 11, and may include, for example, a publicly known sensor of a proximity type by ultrasound, infrared rays, or the like, or a sensor of a contact type capable of detecting that the thumb has been contacted therewith by the change or the like in the electrostatic capacitance.

A constituent material from which the grip 10 may be fabricated is not specifically limited, and can include a publicly known metal material and plastic material. On the side surface (peripheral surface) of the grip 10, an elastically deformable elastic member (illustration is omitted), such as urethane, may be provided. Providing such an elastic member on a grip surface of the grip 10 can reduce a burden to the hand H1 of the patient.

(Grip Actuator)

Figure 3:
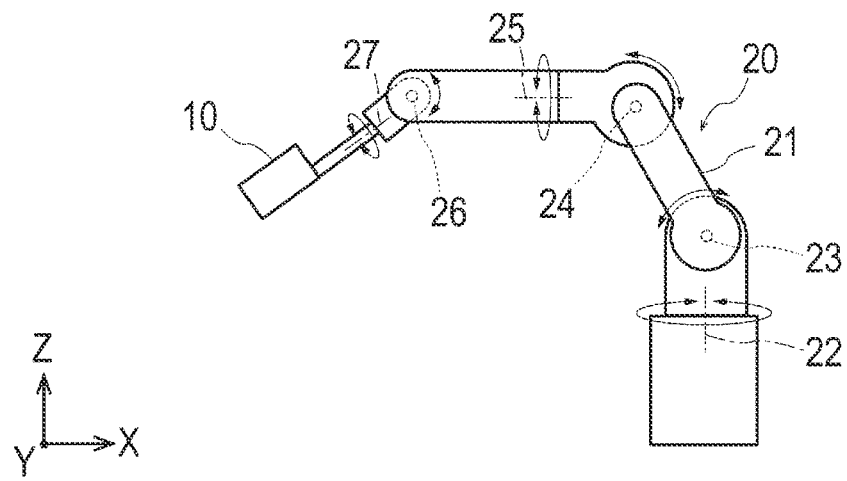
FIG. 3 is a side view illustrating a grip actuator of the puncture system according to the embodiment of the present invention.

The grip actuator 20 is configured, as illustrated in FIG. 3, to hold the grip 10, and be capable of adjusting a position and a posture (orientation) of the grip 10. Herein, "the position of the grip 10" means, as illustrated in FIG. 2, coordinates (Px, Py, Pz) of an arbitrary point P1 (for example, center point) included in the grip 10 in rectangular coordinates of three axes X, Y, and Z. Moreover, "the posture of the grip 10" means angles (Rx, Ry, Rz) around the three axes X, Y, and Z of the grip 10 in the direction (the axis direction a1) along which the fingers other than the thumb are arranged. FIG. 1 illustrates a case where the X axis extends in the left-and-right direction, the Y axis extends in the depth direction, and the Z axis extends in the up-and-down direction, however, the directions of the X axis, the Y axis, and the Z axis are not specifically limited as long as the directions are orthogonal to one another.

The grip actuator 20 includes, in the present embodiment, as illustrated in FIG. 3, a multi-degree-of-freedom robot arm 21 that holds one end of the grip 10.

The robot arm 21 includes a first axis 22, a second axis 23, a third axis 24, a fourth axis 25, a fifth axis 26, and a sixth axis 27. The respective axes 22 to 27 are rotationally driven, for example, by a servomotor. The grip 10 that is disposed at the distal portion of the robot arm 21 has 6 degrees of freedom. In the present specification, the "6 degrees of freedom" means being movable in a direction along the X axis direction, a direction along the Y axis direction, and a direction along the Z axis direction, and rotatable around the X axis, around the Y axis, and around the Z axis. Moreover, the degree of freedom of the robot arm 21 is not limited to the 6 degrees of freedom, and the arrangement of the axes is not specifically limited.

Figure 4A:
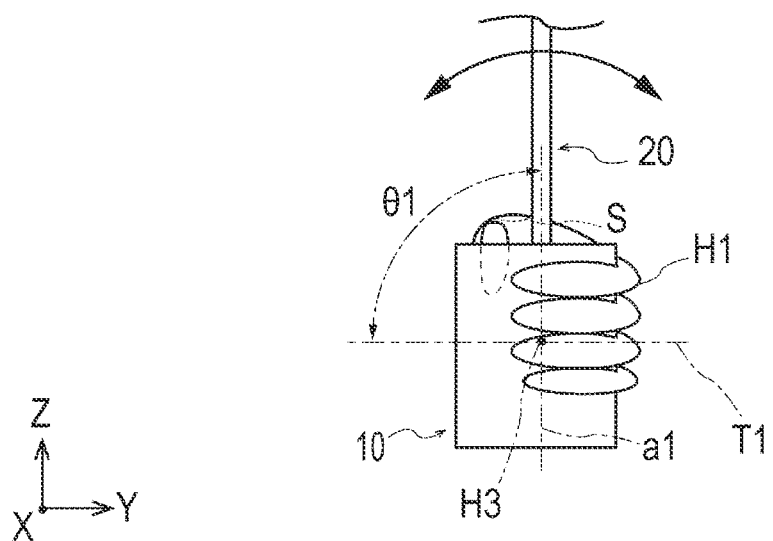
FIG. 4A is a view to be used for an explanation of an operation of the grip actuator of the puncture system according to the embodiment of the present invention.

The robot arm 21 adjusts, for example, the rotation amounts of the respective axes 22 to 27 to allow, as illustrated in FIG. 4A by the solid line arrow, the grip 10 to rotate around a long axis H3 of a forearm H2 using an elbow as a starting point. In this case, a rotary angle of the grip 10 is preferably within a range of a movable region of the elbow. Such a range can include, for example, a range in which an angle θ1 formed by a straight line T1 parallel to the Y axis and the axis direction (axial direction) a1 of the grip 10 is 0 degrees or more and 180 degrees or less. In this manner, the robot arm 21 can rotate the grip 10 around the long axis H3 of the forearm H2 using the elbow as the starting point, and thus can adjust an orientation of an intended or planned puncture region S (a puncture site and a peripheral region thereof) on a body surface of the hand H1.

Figure 4B:
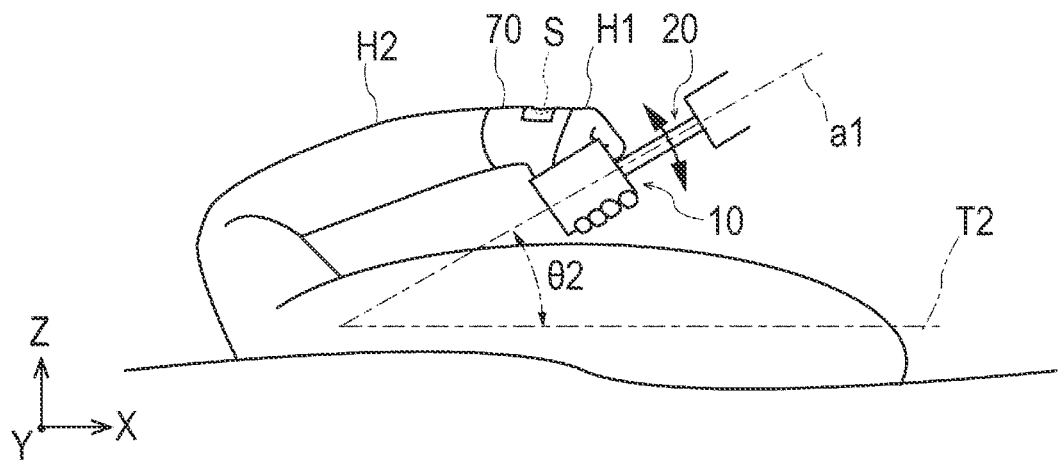
FIG. 4B is a view to be used for an explanation of the operation of the grip actuator of the puncture system according to the embodiment of the present invention.

The robot arm 21 adjusts, for example, the rotation amounts of the respective axes 22 to 27 to allow, as illustrated in FIG. 4B by the solid line arrow, the grip 10 to turn using the elbow as the starting point. In this case, a turn angle of the grip 10 is preferably within the range of the movable region of the elbow. Such a range can include, for example, in a case where a direction separated from the abdominal region using a straight line T2 as a reference is + (plus), a range in which an angle θ2 formed by the straight line T2 parallel to the X axis and the axis direction a1 of the grip 10 becomes −45 degrees or more and +90 degrees or less, and more preferably, a range of 0 degrees or more and +45 degrees or less. Accordingly, in a state where the patient has gripped the grip 10, the robot arm 21 can cause the grip 10 to approach and separate from the body using the elbow as the starting point.

The grip actuator 20 is configured so as to be switchable between two modes, namely a free adjustment mode in which the position and the posture of the grip 10 are adjustable together with an operation of the patient, and a forced mode in which the position and the posture of the grip 10 are forcedly adjusted in accordance with an instruction by a control unit 81.

The configuration of the grip actuator 20 is not specifically limited as long as a posture in at least one direction of the grip 10 is adjustable. For example, the grip actuator 20 may include, not the robot arm 21, but a rotation mechanism capable of turning the grip 10.

(Blood Vessel Detection Unit)

The blood vessel detection unit 30 is configured so as to be capable of detecting a position of the radial artery V of the hand H1 that grips the grip 10. In addition, in the present embodiment, the blood vessel detection unit 30 further detects a depth (distance from the body surface to the blood vessel) of the radial artery V, and a position and the like of tissue (hereinafter, referred to as a surrounding tissue) such as a tendon and a bone in the surrounding region of the radial artery V.

Figure 5:
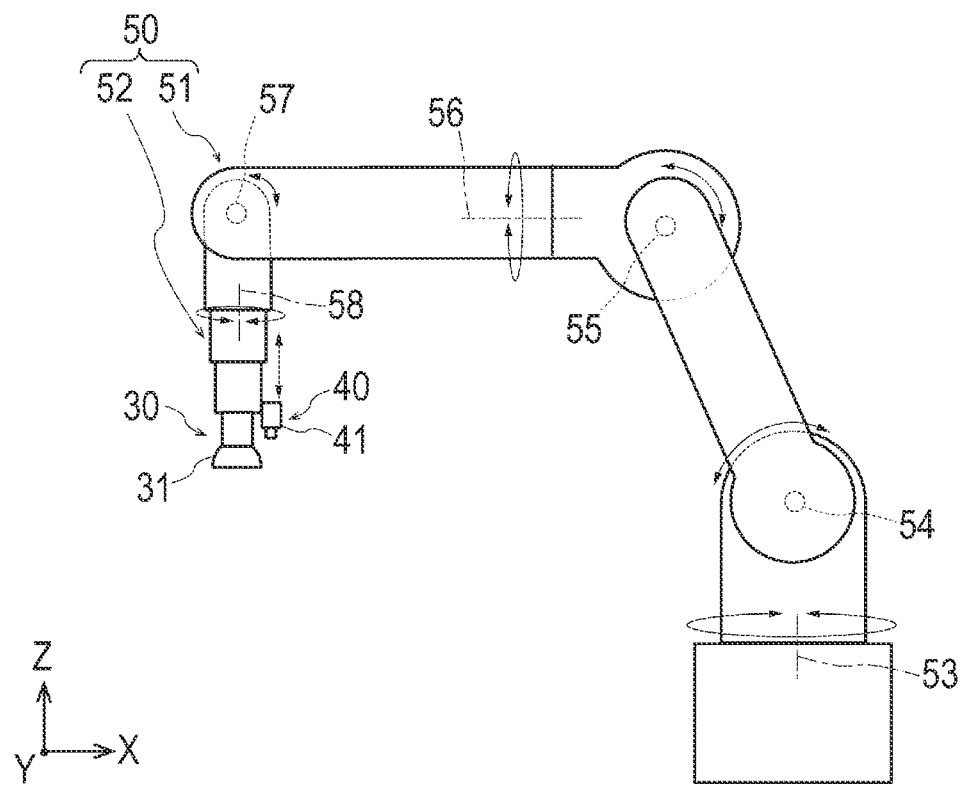
FIG. 5 is a side view illustrating a detection actuator of the puncture system according to the embodiment of the present invention.

The blood vessel detection unit 30 includes, in the present embodiment, as illustrated in FIG. 5, an ultrasound wave echo 31. The blood vessel detection unit 30 is not specifically limited as long as it is capable of detecting a position of the radial artery V, and may include, for example, an infrared ray camera.

(Reversed Blood Detection Unit)

The reversed blood detection unit 40 is configured to be capable of detecting blood (reversed blood) flowing into the puncture needle N when the radial artery V has been punctured. The reversed blood detection unit 40 includes, in the present embodiment, as illustrated in FIG. 5, a camera 41 that detects reversed blood to the puncture needle N. The reversed blood detection unit 40 is not specifically limited as long as it is capable of detecting reversed blood to the puncture needle N. For example, the reversed blood detection unit 40 can include a pressure sensor or the like capable of measuring change in the internal pressure of the puncture needle N due to the reversed blood.

The camera 41 also functions as a marker detection unit that detects a circumferential edge portion 72 (see FIG. 9) of the restrainer 70 that functions as a marker indicating the intended or planned puncture region S, in the present embodiment. The blood vessel detection unit 30 detects a position and the like of the radial artery V in the intended puncture region S indicated by the circumferential edge portion 72 detected by the camera 41.

(Detection Actuator)

The detection actuator 50 is configured, as illustrated in FIG. 5, to hold the blood vessel detection unit 30 and the reversed blood detection unit 40, and be capable of adjusting a position and a posture of the blood vessel detection unit 30, and a position and a posture of the reversed blood detection unit 40. Herein, the "position of the blood vessel detection unit 30 (the reversed blood detection unit 40)" means coordinates of an arbitrary point included in the blood vessel detection unit 30 (the reversed blood detection unit 40), in the rectangular coordinates of the three axes X, Y, and Z. Moreover, the "posture of the blood vessel detection unit 30 (the reversed blood detection unit 40)" means an angle around the three axes X, Y, and Z of the blood vessel detection unit 30 (the reversed blood detection unit 40).

The detection actuator 50 includes, in the present embodiment, as illustrated in FIG. 5, a multi-degree-of-freedom robot arm 51, and a direct-motion mechanism 52 that is provided to a distal portion of the robot arm 51.

The robot arm 51 includes a first axis 53, a second axis 54, a third axis 55, a fourth axis 56, a fifth axis 57, and a sixth axis 58. The respective axes 53 to 58 are rotationally driven, for example, by a servomotor. The robot arm 51 has 6 degrees of freedom. The degree of freedom of the robot arm 51 is not limited to 6 degrees of freedom, and the arrangement of the axes is not specifically limited.

Figure 6:
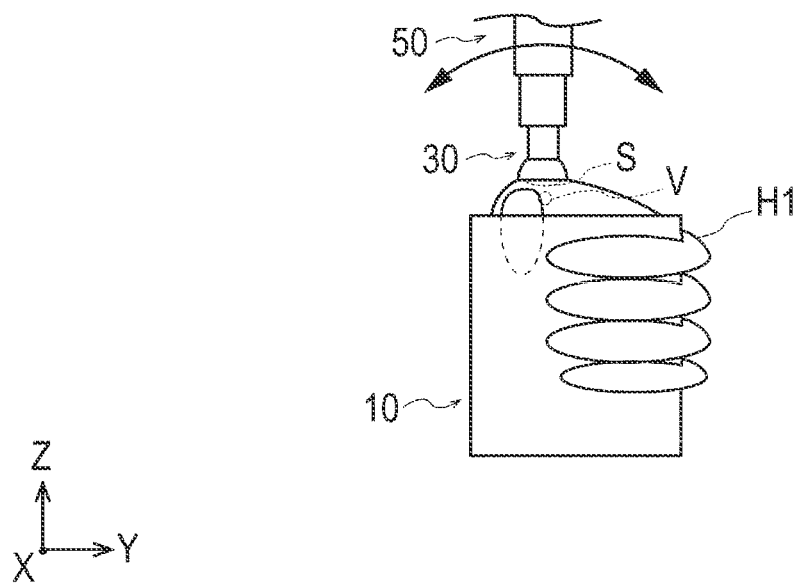
FIG. 6 is a view to be used for an explanation of an operation of the detection actuator of the puncture system according to the embodiment of the present invention.

The robot arm 51 adjusts, for example, the rotation amounts of the respective axes 53 to 58 to allow, as illustrated in FIG. 6 by solid arrows, the blood vessel detection unit 30 to move in a circumferential direction of the radial artery V of the hand H1.

The direct-motion mechanism 52 holds, as illustrated in FIG. 5, the blood vessel detection unit 30 and the reversed blood detection unit 40, and causes the blood vessel detection unit 30 and the reversed blood detection unit 40 to move forward and backward. The direct-motion mechanism 52 can be configured by a publicly known direct-motion mechanism such as a linear bush, a cylinder stroke, and a ball screw. Herein, "move forward" indicates that the blood vessel detection unit 30 (the reversed blood detection unit 40) is caused to move in a direction approaching the grip 10, and "move backward" indicates that the blood vessel detection unit 30 (the reversed blood detection unit 40) is caused to move in a direction separating from the grip 10.

The configuration of the detection actuator 50 is not specifically limited as long as the detection actuator 50 is capable of moving at least the blood vessel detection unit 30 forward and backward toward the grip 10. For example, the detection actuator 50 may include, not the robot arm 51, but only the direct-motion mechanism 52. Moreover, for example, the detection actuator 50 may adjust the posture of the blood vessel detection unit 30, not by the robot arm 51, but by a rotation mechanism capable of turning the blood vessel detection unit 30.

(Puncture Actuator)

The puncture actuator 61 is operatively connected to the forward mechanism 62 and is configured to be capable of adjusting a position and a posture of the puncture needle N. Herein, the "position of the puncture needle N" means coordinates of an arbitrary point included in the puncture needle N, in the rectangular coordinates of the three axes X, Y, and Z. Moreover, the "posture of the puncture needle N" means an angle around the three axes X, Y, and Z in the longitudinal direction of the elongated puncture needle N.

Figure 7:
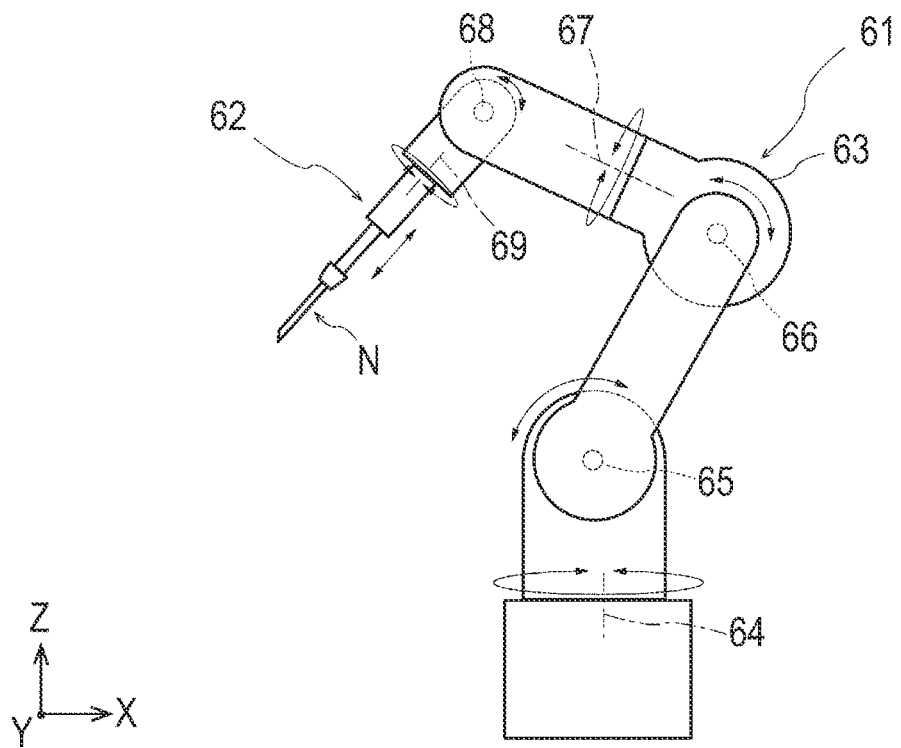
FIG. 7 is a side view illustrating a puncture actuator and a forward mechanism of the puncture system according to the embodiment of the present invention.

The puncture actuator 61 includes, in the present embodiment, as illustrated in FIG. 7, a multi-degree-of-freedom robot arm 63.

The robot arm 63 includes a first axis 64, a second axis 65, a third axis 66, a fourth axis 67, a fifth axis 68, and a sixth axis 69. The respective axes 64 to 69 are rotationally driven, for example, by a servomotor. The robot arm 63 has 6 degrees of freedom. The degree of freedom of the robot arm 63 is not limited to 6 degrees of freedom, and the arrangement of the axes is not specifically limited.

The robot arm 63 can adjust, for example, by adjusting the rotation amounts of the respective axes 64 to 69, as illustrated in FIG. 8A by the solid line arrow, an angle θ3 (puncture angle) formed by a tangent plane T3 of an intended or planned puncture site P2 on the body surface of the hand H1 and the puncture needle N. The puncture angle θ3 is not specifically limited, and is preferably 30 degrees or more and 45 degrees or less.

The robot arm 63 can be adjusted, for example, by adjusting the rotation amounts of the respective axes 64 to 69 to allow, as illustrated in FIG. 8B, the posture of the puncture needle N such that the puncture needle N is punctured into the radial artery V along an extending direction of the radial artery V as much as possible.

The configuration of the puncture actuator 61 is not specifically limited as long as a posture in at least one direction of the puncture needle N is adjustable. For example, the puncture actuator 61 may include, not the robot arm 63, but a rotation mechanism capable of turning the puncture needle N.

(Forward Mechanism)

The forward mechanism (puncture needle holder) 62 holds, as illustrated in FIG. 7, the puncture needle N, and causes the puncture needle N to move forward and backward.

The forward mechanism 62 is provided at a distal portion of the puncture actuator 61. The forward mechanism 62 can be configured by a publicly known direct-motion mechanism such as a linear bush, a cylinder stroke, and a ball screw. Herein, "move forward" indicates that the puncture needle N is caused to move in a direction approaching the grip 10, and "move backward" indicates that the puncture needle N is caused to move in a direction separating from the grip 10.

(Restrainer)

Figure 9:
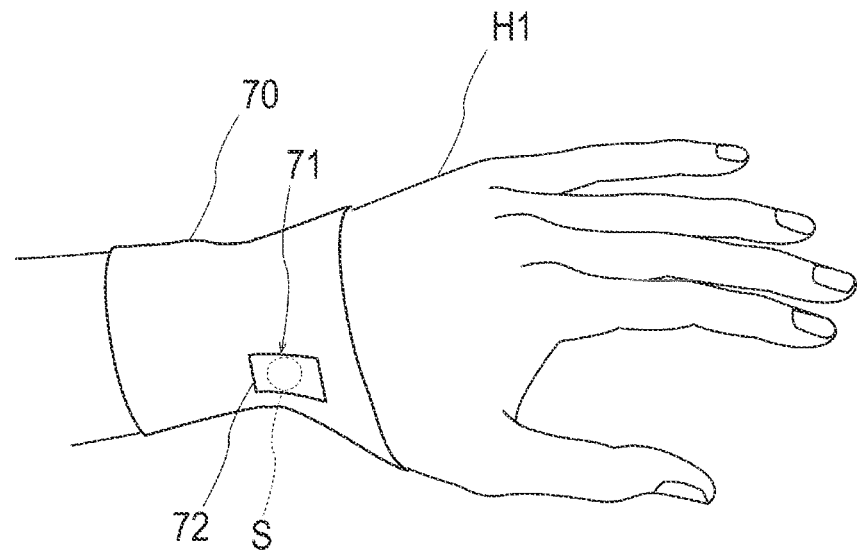
FIG. 9 is a perspective view illustrating a restrainer of the puncture system according to the embodiment of the present invention.

The restrainer 70 is configured, as illustrated in FIG. 9, so as to suppress a motion of a wrist of the patient.

The restrainer 70 includes, in the present embodiment, an annular member, a band (e.g., band-like member), or the like that causes fingers to be exposed and surrounds the wrist. The restrainer 70 is not specifically limited as long as it can suppress the motion of the wrist of the patient, and may include, for example, a glove or the like that covers the fingers.

The restrainer 70 includes an opening portion 71 that allows the intended puncture region S of the hand H1 to be exposed. The circumferential edge portion 72 of the opening portion 71 functions as a marker indicating the intended puncture region S by surrounding the intended puncture region S. The circumferential edge portion 72 is not specifically limited as long as it is capable of being detected by the camera 41, and is preferably blue color so as to be easily determined as an element or feature other than the living body.

FIG. 9 illustrates an example in which a snuff box is exposed as the intended puncture region S through the opening portion 71. Further, the position of the opening portion 71 is changeable as appropriate in accordance with the position of the intended puncture region S.

(Control Unit)

Figure 10:
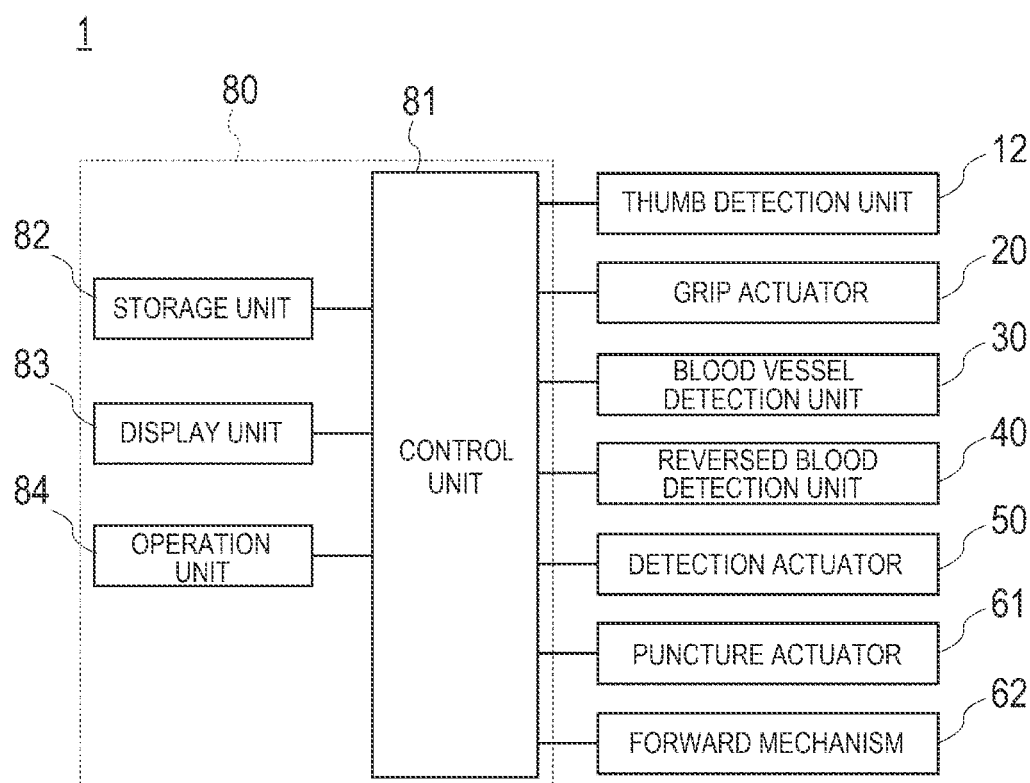
FIG. 10 is a block diagram of the puncture system according to the embodiment of the present invention.

The control unit 80 is provided with, as illustrated in FIGS. 1 and 10, the control unit 81, a storage unit 82, a display unit 83, and an operation unit 84. Hereinafter, a configuration of each unit will be described.

The control unit 81 includes a central processing unit (CPU). The control unit 81 controls operations of the thumb detection unit 12, the grip actuator 20, the blood vessel detection unit 30, the reversed blood detection unit 40, the detection actuator 50, the puncture actuator 61, the forward mechanism 62, the storage unit 82, the display unit 83, and the operation unit 84.

The control unit 81 determines a relative posture of the grip 10 and the puncture needle N and a forward distance in accordance with the position of the radial artery V detected by the blood vessel detection unit 30, and controls operations of the adjustment mechanism 2 (the grip actuator 20, the puncture actuator 61) and the forward mechanism 62 on the basis of the determined posture and forward distance.

Specifically, in the present embodiment, the control unit 81 determines a position and a posture of the grip 10 in accordance with the position of the radial artery V detected by the blood vessel detection unit 30, and controls an operation of the grip actuator 20 such that the grip 10 moves to the determined position and has the determined posture. Moreover, the control unit 81 determines a standby position (position at which the puncture needle N, before moving forward, is separated from the hand H1 that grips the grip 10) and a posture of the puncture needle N, in accordance with the position of the radial artery V detected by the blood vessel detection unit 30, and controls an operation of the puncture actuator such that the puncture needle N moves to the standby position and has the determined posture. The control unit 81 determines a forward distance in accordance with the position of the radial artery V detected by the blood vessel detection unit 30, and controls an operation of the forward mechanism 62 such that the puncture needle N moves forward from the standby position by the determined forward distance.

The control unit 81 may determine a relative position and a relative posture of the grip 10 and the puncture needle N, a forward distance of the puncture needle N, and the like by considering not only the position of the radial artery V but also the depth of the radial artery V, the position of the surrounding tissue, and the like. Moreover, the control unit 81 may extract a plurality of candidates (possibilities) for the relative position and the relative posture of the grip 10 and the puncture needle N, and may select an optimal position and an optimal posture among the plurality of the candidates by considering the position of the radial artery V, the depth of the radial artery V, the position of the surrounding tissue, and the like.

The control unit 81 acquires data on positions and postures of the grip 10, the grip actuator 20, the blood vessel detection unit 30, the reversed blood detection unit 40, the detection actuator 50, the puncture needle N, the puncture actuator 61, and the forward mechanism 62. The control unit 81 may acquire data on a position and a posture of each component, by providing a publicly known sensor capable of detecting a position and a posture to each component, from the sensor. Moreover, data on a position and a posture of each component may be calculated from data on the size of each component and data on the drive amount of each component. The control unit 81 controls, on the basis of the data on the position and the posture of each component, operations of the grip actuator 20, the detection actuator 50, the puncture actuator 61, and the forward mechanism 62 such that the components are not interfered with each other.

The storage unit 82 includes a read only memory (ROM) that stores therein various kinds of programs and various kinds of data, a random access memory (RAM) that temporarily stores therein a program and data as a work region, a hard disk that stores therein various kinds of programs including an operating system and various kinds of data, and the like.

The storage unit 82 stores therein a puncture program for automatically puncturing the radial artery V of the hand H1, and various kinds of data to be used with the execution of the puncture program. The puncture program may be provided by a computer-readable recording medium, or may be downloaded from the Internet. The recording medium is not specifically limited as long as it is readable by the computer, and may include, for example, an optical disk such as a CD-ROM or a DVD-ROM, a USB memory, an SD memory card, and the like.

The display unit 83 can include, for example, a liquid crystal display. The display unit 83 is used for displaying information for automatically puncturing the radial artery V of the hand H1.

The operation unit 84 can include, for example, a pointing device such as a mouse, a key board, and the like. The operation unit 84 is used for performing an input for automatically puncturing the radial artery V of the hand H1.

The configurations of the display unit 83 and the operation unit 84 are not limited to the above-mentioned configurations. For example, the display unit 83 and the operation unit 84 may be integrally configured as a touch panel.

(Puncture Method)

Figure 11:
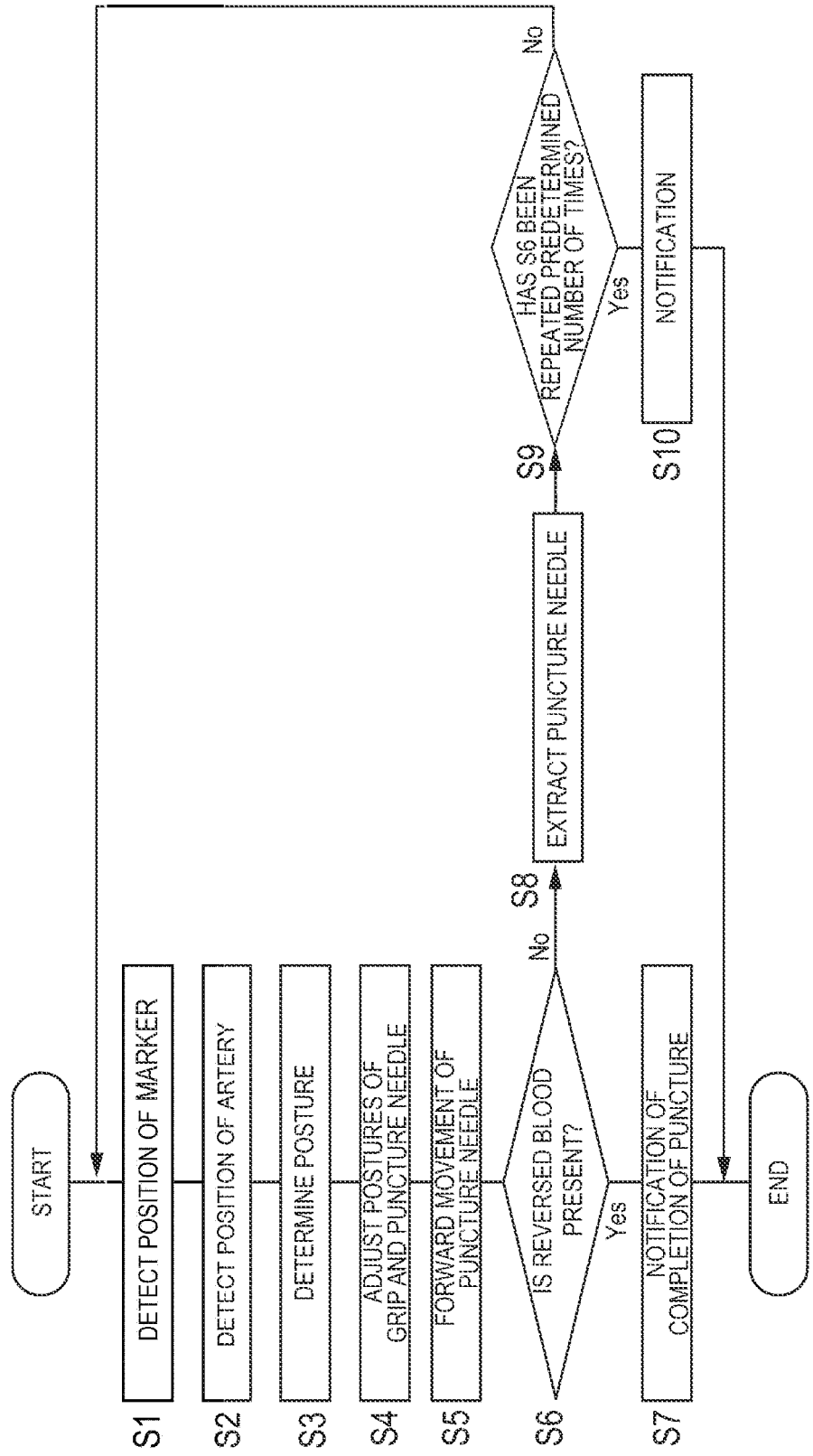
FIG. 11 is a flowchart illustrating a puncture method by the puncture system according to the embodiment of the present invention.

FIG. 11 illustrates a puncture method using the puncture system 1. Next, the puncture method using the puncture system 1 will be described.

Firstly, a patient lies on his/her back on the operating table D as illustrated in FIG. 1, and grips the grip 10 with his/her hand H1, while the restrainer 70 is mounted on the patient's hand H1, in a state where the patient's hand H1 is disposed on an abdominal region. In this case, the grip actuator 20 is in the free adjustment mode, so that the patient can take a comfortable posture for himself/herself. Next, an operator disinfects the periphery of the intended puncture region S, and anesthetizes the patient. In the subsequent Step, the restrainer 70 can hold or maintain the posture of the hand H1 constant. Accordingly, the restrainer 70 can prevent a careless or unintended position shift of the radial artery V because the wrist moves carelessly or unintentionally.

Next, the control unit 81 causes, as illustrated in FIG. 11, the camera 41 to detect the circumferential edge portion 72 of the restrainer 70 that functions as a marker indicating the intended puncture region S of the hand H1 (Step S1). In this case, the control unit 81 may cause the grip actuator 20 and the detection actuator 50 to adjust a relative position and a relative posture of the grip 10 and the camera 41 so as to allow the camera 41 to detect the circumferential edge portion 72.

Next, in the intended puncture region S indicated by the circumferential edge portion 72 of the restrainer 70, the control unit 81 causes the blood vessel detection unit 30 to detect a position and a depth of the radial artery V, a position of the surrounding tissue, and the like (Step S2). In this manner, a test range of the blood vessel detection unit 30 is limited to allow detection of a position of the radial artery V with increased efficiency. In the present embodiment, the blood vessel detection unit 30 includes the ultrasound wave echo 31, so that as illustrated in FIG. 6, the detection is performed by pressing the ultrasound wave echo 31 against the intended puncture region S on the body surface of the hand H1. In this case, the control unit 81 may cause the grip actuator 20 and the detection actuator 50 to adjust a relative position and a relative posture of the grip 10 and the blood vessel detection unit 30 so as to allow the blood vessel detection unit 30 to detect a position of the radial artery V. After the detection has been completed, the control unit 81 instructs the detection actuator 50 to cause the blood vessel detection unit 30 to move backward.

Next, the control unit 81 determines, as illustrated in FIG. 11, on the basis of the position and the depth of the radial artery V, the position of the surrounding tissue, and the like detected at Step S2, a position and a posture of the grip 10, and a posture, a standby position, and a forward distance of the puncture needle N (Step S3).

Next, the control unit 81 causes the grip actuator 20 to adjust the position and the posture of the grip 10 such that the grip 10 moves to the position determined at Step S3, and has the posture determined at Step S3. Moreover, the control unit 81 causes the puncture actuator 61 to adjust the position and the posture of the puncture needle N such that the puncture needle N moves to the standby position determined at Step S3, and has the posture determined at Step S3 (Step S4).

Next, the control unit 81 instructs the puncture actuator 61 to cause the puncture needle N to move forward by the forward distance determined at Step S3 from the standby position (Step S5). Therefore, the puncture needle N punctures the living body.

Next, the control unit 81 checks whether reversed blood to the puncture needle N is present by the reversed blood detection unit 40 (Step S6).

If having checked that the reversed blood to the puncture needle N is present at Step S6 (Step S6; Yes), the control unit 81 notifies the operator that the puncture has been normally completed (Step S7). Next, the operator performs subsequent therapeutic procedures such as the insertion of a guide wire and a sheath and the like, via a lumen of the puncture needle N. In a case where the puncture system 1 is configured such that the guide wire can be inserted into the lumen of the puncture needle N, the puncture system 1 may perform the insertion of the guide wire and the like. Moreover, after the puncture needle N is extracted, the control unit 81 may cause the grip actuator 20 to adjust the position and the posture of the grip 10 such that the operator easily performs surgery.

If having checked that no reversed blood to the puncture needle N is present at Step S6 (Step S6; No), the control unit 81 instructs the puncture actuator 61 to move the puncture needle N backward, and to extract the puncture needle N to the outside of the living body (i.e., to withdraw the needle from the living body) (Step S8).

Next, the control unit 81 determines whether Step S6 has been repeated a predetermined number of times (Step S9).

If having determined that Step S6 has not been repeated a predetermined number of times at Step S9 (Step S9; No), the control unit 81 again executes Steps S1 to S8. In a case where the control unit 81 is configured to extract a plurality of candidates or possibilities for a relative position and a relative posture of the grip 10 and the puncture needle N, the control unit 81 may select a candidate or possibility other than the candidate or possibility selected the first time, at Step S3 at the second time and subsequent times.

If having determined that S6 has been repeated the predetermined number of times at Step S9 (Step S9; Yes), the control unit 81 notifies the operator that an error occurs, and the puncture is shifted to the puncture by the operator (Step S10). The notification may be made with the display unit 83, or may be made with a speaker or the like.

At the abovementioned Steps S1 to S9, when the thumb detection unit 12 has detected that the thumb is not disposed in the hole portion 11, the control unit 81 may stop the operations of the respective units, and may provide a notification of an error.

As has been described in the foregoing, the puncture system 1 according to the abovementioned embodiment is a puncture system capable of automatically puncturing the radial artery V of the hand H1 of the patient. The puncture system 1 includes the grip 10 to be gripped by the hand H1, the blood vessel detection unit 30 configured to detect a position of the radial artery V of the hand H1 that grips the grip 10, the adjustment mechanism 2 configured to adjust a relative posture of the grip 10 and the puncture needle N, the forward mechanism 62 configured to move the puncture needle N forward toward the grip 10, and the control unit 81 that determines, in accordance with the position of the radial artery V detected by the blood vessel detection unit 30, a relative posture of the grip 10 and the puncture needle N and a forward distance of the puncture needle N, and controls operations of the adjustment mechanism 2 and the forward mechanism 62 on the basis of the posture and the forward distance having been determined. Accordingly, the abovementioned puncture system 1 is configured to puncture a blood vessel of the hand H1 by adjusting the posture of the puncture needle N in accordance with the posture of the hand H1. Moreover, the puncture system 1 allows the automatic puncture, and thus can perform stable puncture independent of the degree of proficiency of the operator. Moreover, the operator does not need to perform puncture, and thus can perform other work during the puncture.

Moreover, the adjustment mechanism 2 includes the grip actuator 20 configured to adjust the posture of the grip 10. Accordingly, the puncture system 1 can adjust the posture of the hand H1 that grips the grip 10, by the grip actuator 20.

Moreover, the adjustment mechanism 2 includes the puncture actuator 61 configured to adjust the posture of the puncture needle N. Accordingly, the puncture system 1 can adjust the posture of the puncture needle N, by the puncture actuator 61.

Moreover, the adjustment mechanism 2 includes the grip actuator 20 configured to adjust a position and a posture of the grip 10, and the puncture actuator 61 configured to adjust a position and a posture of the puncture needle N, and the control unit 81 acquires data on the position and the posture of the grip 10, and data on the position and the posture of the puncture needle N. Accordingly, the puncture system 1 can cause the hand H1 to have various postures by adjusting the posture of the hand H1 that grips the grip 10 by the grip actuator 20, and can perform puncture to the hand H1 in the various postures by adjusting the posture of the puncture needle N by the puncture actuator 61.

Moreover, the puncture system 1 further includes the reversed blood detection unit 40 configured to detect reversed blood to the puncture needle N. Accordingly, the puncture system 1 can easily grasp whether the puncture to the radial artery V has been completed.

Moreover, the puncture system 1 further includes the camera 41 configured to detect a position of the circumferential edge portion 72 indicating the intended puncture region S of the hand H1. The blood vessel detection unit 30 detects the radial artery V in the intended puncture region S. Accordingly, the puncture system 1 can efficiently detect the position of the radial artery V.

Moreover, the puncture system 1 further includes the detection actuator 50 that holds the blood vessel detection unit 30, and is configured to adjust a position and a posture of the blood vessel detection unit 30. Accordingly, the puncture system 1 can easily detect a position of the radial artery V by adjusting the position and the posture of the blood vessel detection unit 30.

Moreover, in the grip 10, the hole portion 11 into which a thumb of the hand H1 is inserted is formed, and in the hole portion 11, the thumb detection unit 12 that detects a state where the thumb has been contacted therewith is disposed. Accordingly, the puncture system 1 can determine whether the thumb is disposed to an adequate position in the grip 10.

Moreover, the puncture system 1 includes the restrainer 70 that suppresses the motion of the wrist of the patient. Accordingly, it is possible to determine the posture of the hand H1 that grips the grip 10 constant.

(Modification Example of Puncture Method)

Figure 12A:
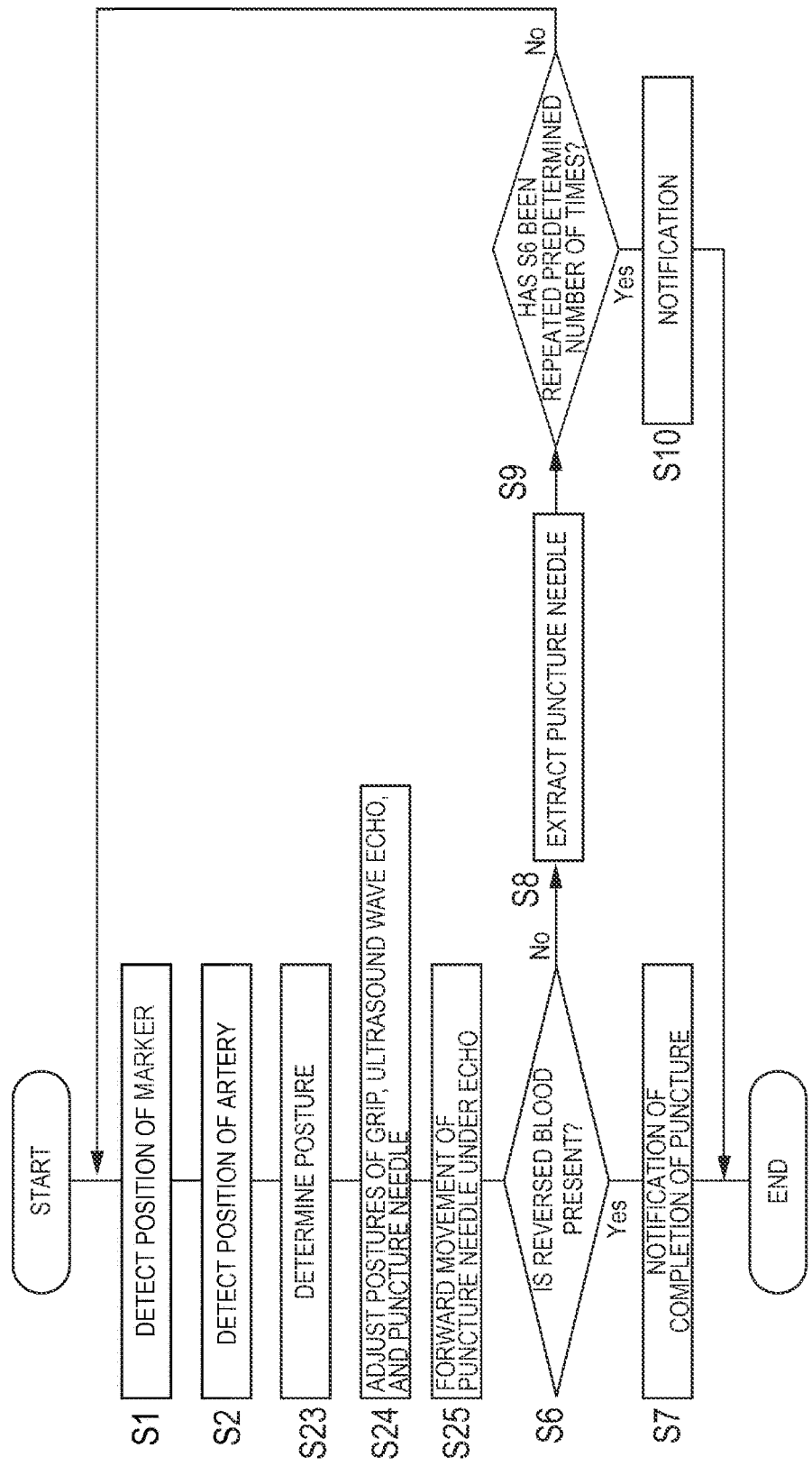
FIG. 12A is a flowchart illustrating a puncture method according to a modification example.
Figure 12B:
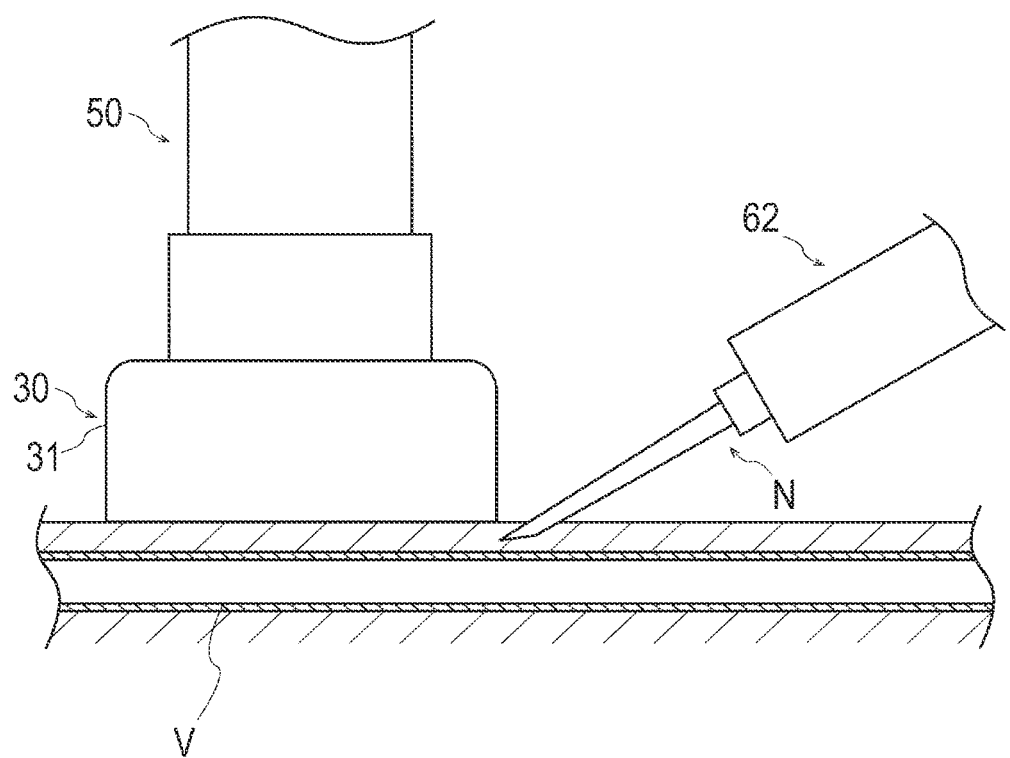
FIG. 12B is a view to be used for an explanation of the puncture method illustrated in FIG. 12A.

FIGS. 12A and 12B illustrate a modification example of a puncture method by the puncture system 1.

In the puncture method according to the modification example, as illustrated in FIG. 12A, Steps from the position detection of the marker (Step S1) to the position detection of the radial artery V (Step S2) are similar to those in the puncture method according to the abovementioned embodiment. Accordingly, the explanation of Steps S1 to S2 is not repeated in detail omitted.

After Step S2, the control unit 81 determines, on the basis of the position and the depth of the radial artery V, the position of the surrounding tissue, and the like detected at Step S2, a position and a posture of the grip 10, a posture, a standby position, and a forward distance of the puncture needle N, and a position and a posture of the blood vessel detection unit 30 (Step S23).

Next, the control unit 81 causes the grip actuator 20 to adjust the position and the posture of the grip 10 such that the grip 10 moves to the position determined at Step S23, and has the posture determined at Step S23. Moreover, the control unit 81 causes the puncture actuator 61 to adjust the position and the posture of the puncture needle N such that the puncture needle N moves to the standby position determined at Step S23, and has the posture determined at Step S23. Moreover, the control unit 81 causes the detection actuator 50 to adjust the position and the posture of the blood vessel detection unit 30 such that the blood vessel detection unit 30 moves to the position determined at Step S23, and has the posture determined at Step S23 (Step S24).

Next, the control unit 81 causes, as illustrated in FIGS. 12A and 12B, the puncture needle N to move forward from the standby position, and the ultrasound wave echo 31 of the blood vessel detection unit 30 to simultaneously detect positions of the radial artery V and a distal portion of the puncture needle N (Step S25). In this case, the control unit 81 may change the test range by moving the ultrasound wave echo 31 of the blood vessel detection unit 30 in the circumferential direction of the radial artery V (see FIG. 6). Therefore, the blood vessel detection unit 30 can easily grasp or determine a positional relationship between the radial artery V and the puncture needle N.

The control unit 81 instructs the puncture actuator 61 to adjust (correct), in accordance with the positions of the radial artery V and the distal portion of the puncture needle N detected by the ultrasound wave echo 31, the position, the posture, and the forward distance of the puncture needle N. Accordingly, it is possible to adjust the posture of the puncture needle N even in a case where the radial artery V has moved so as to avoid or escape puncture by the puncture needle N when the puncture needle N has been inserted into the living body and other cases.

The puncture needle N is preferably an echo needle (needle that includes a groove or a hole portion being formed at the distal portion thereof, and irregularly reflects ultrasound) easily detectable by the ultrasound wave echo 31, but does not need to be an echo needle.

Subsequent Steps S6 to S10 (see FIG. 12A) are the same as those in the puncture method according to the abovementioned embodiment, and thus the explanation thereof is not repeated (see FIG. 11). At Step S24 in place of Step S6, the ultrasound wave echo 31 may check whether the puncture needle N has reached the radial artery V, and reversed blood to the puncture needle N has occurred.

As has been described in the foregoing, in the puncture method according to the modification example, the blood vessel detection unit 30 simultaneously detects positions of the radial artery V and the puncture needle N, and the puncture actuator 61 adjusts the posture of the puncture needle, in accordance with the positions of the radial artery V and the puncture needle N detected by the blood vessel detection unit 30. Accordingly, it is possible to adjust the posture of the puncture needle N, for example, even in a case where the radial artery V has moved so as to avoid or escape puncture by the puncture needle N when the puncture needle N has been inserted into the living body and other cases.

(Modification Examples of Grip)

Figure 13A:
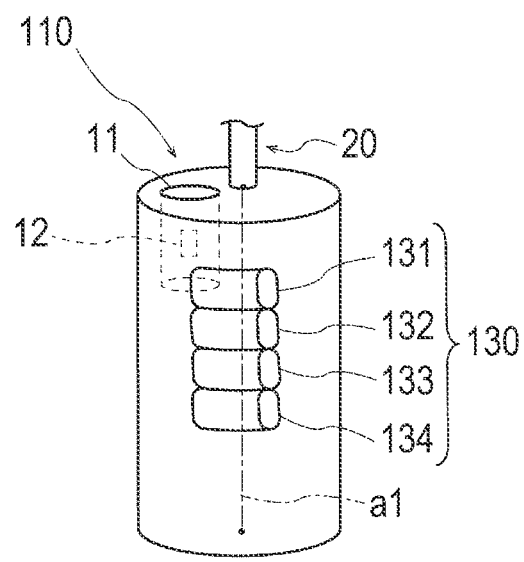
FIG. 13A is a perspective view illustrating a grip according to a first modification example.
Figure 13B:
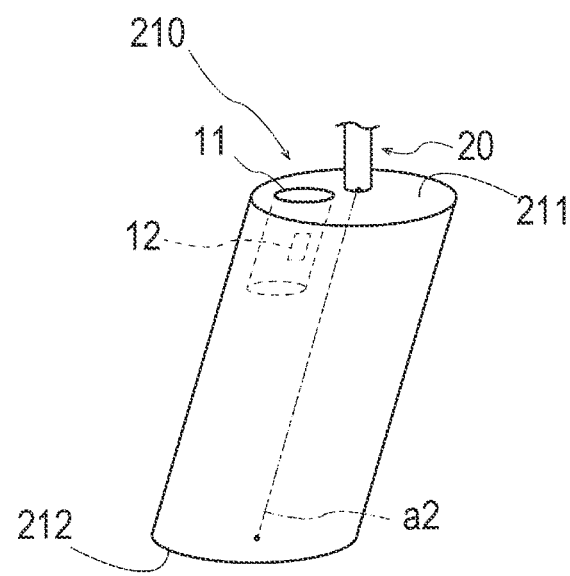
FIG. 13B is a perspective view illustrating a grip according to a second modification example.
Figure 13C:
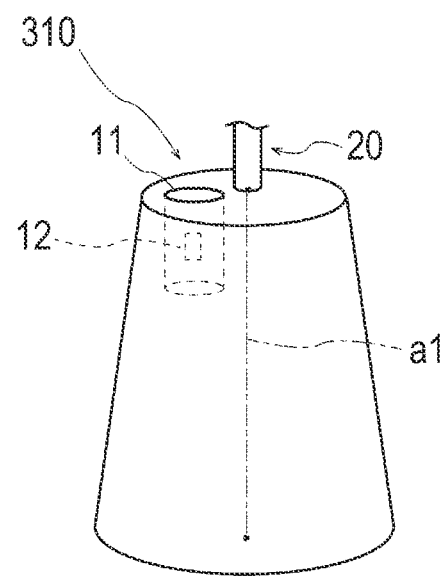
FIG. 13C is a perspective view illustrating a grip according to a third modification example.

FIGS. 13A to 13C illustrate grips 110, 210, and 310 according to first to third modification examples. In the following explanation, configurations and features similar to those in the puncture system 1 according to the abovementioned embodiment are assigned the same reference numerals, and a detailed explanation thereof is not repeated.

The grip 110 according to the first modification example is different from the grip 10 according to the abovementioned embodiment in that the grip 110 includes an insertion unit 130 that allows the fingers other than the thumb to be inserted, as illustrated in FIG. 13A. The insertion unit 130 includes, in this embodiment shown by way of example, a first pocket 131 into which a forefinger is capable of being inserted, a second pocket 132 into which a middle finger is capable of being inserted, a third pocket 133 into which a ring finger is capable of being inserted, and a fourth pocket 134 into which a little finger is capable of being inserted. Further, the configuration of the insertion unit 130 is not specifically limited as long as the fingers other than the thumb are capable of being inserted. For example, the insertion unit 130 may be configured as a single pocket that allows all of the forefinger, the middle finger, the ring finger, and the little finger to be inserted.

In this manner, the grip 110 according to the first modification example includes the insertion unit 130 that allows the fingers other than the thumb to be inserted. Accordingly, even in a state where the patient is anesthetized and other states, the state where the hand H1 has gripped the grip 110 can be easily maintained.

The grip 210 according to the second modification example is different from the grip 10 according to the abovementioned embodiment in that the grip 210 has an inclined cylindrical shape, as illustrated in FIG. 13B. The "inclined cylindrical shape" herein means a shape in which when viewed from a direction orthogonal to an end surface 211 of the cylinder, an axis direction a2 is inclined such that center positions of the facing end surfaces 211 and 212 of the cylinder are shifted.

In this manner, the grip 210 according to the second modification example has an inclined cylindrical shape. Accordingly, in a state where the fingers other than the thumb have gripped the grip 210, the patient can easily dispose or position the thumb in the hole portion 11.

The grip 310 according to the third modification example is different from the grip 10 according to the abovementioned embodiment in that the grip 310 has a truncated conical shape, as illustrated in FIG. 13C. In this manner, the grip 310 according to the modification example has a truncated conical shape, so that in a state where the fingers other than the thumb have gripped the grip 310, the patient can easily dispose or position the thumb in the hole portion 11.

As has been described in the foregoing, the shape of the grip is not specifically limited as long as the patient can grip the grip with the hand H1. Moreover, the insertion unit 130 illustrated in FIG. 13A may be provided to each of the grips 210 and 310 according to the second and third modification examples illustrated in FIGS. 13B and 13C.

(Modifications Example of Restrainer)

Figure 14A:
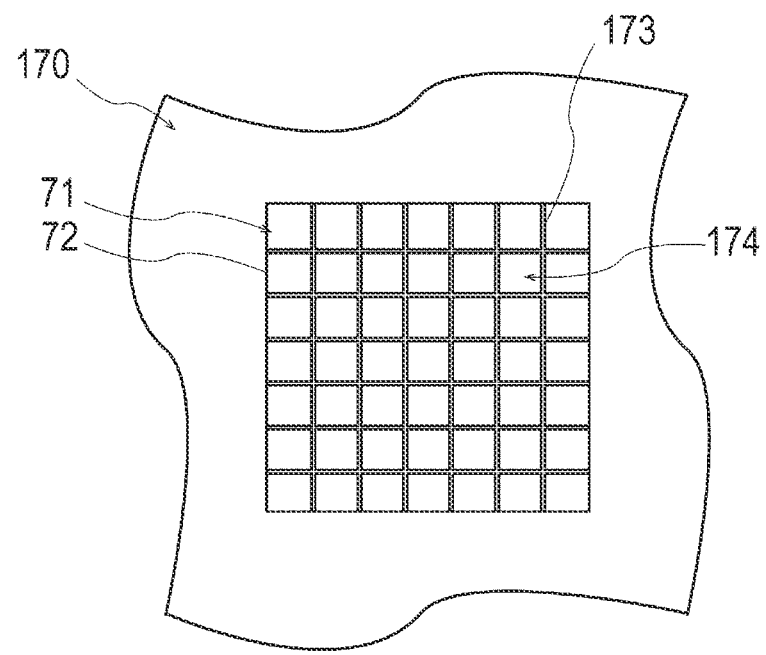
FIG. 14A is a view illustrating a periphery of an opening portion of a restrainer according to a first modification example.
Figure 14B:
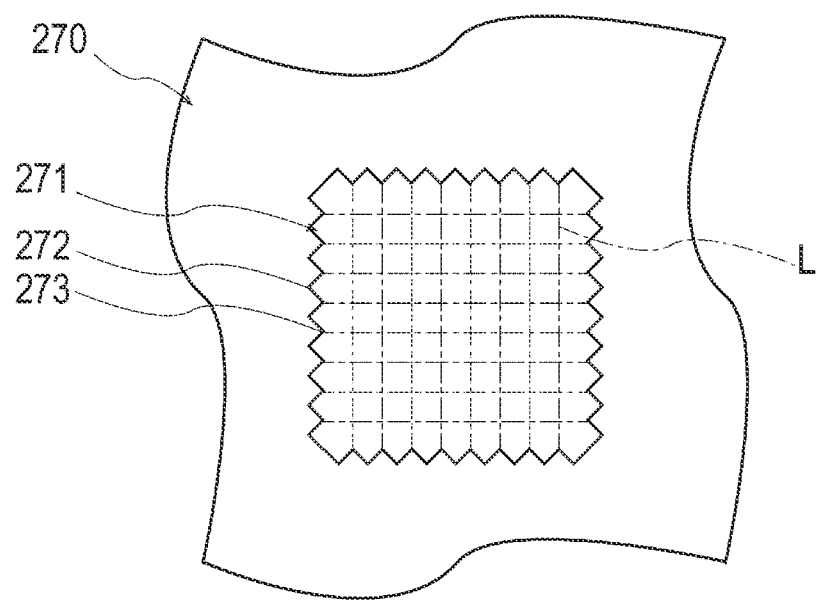
FIG. 14B is a view illustrating a periphery of an opening portion of a restrainer according to a second modification example.

FIGS. 14A and 14B illustrate restrainers 170 and 270 according to first and second modification examples.

The restrainer 170 according to the first modification example can include, similar to the restrainer 70 according to the abovementioned embodiment, an annular member, a band or band body, or the like that surrounds at least the wrist. The restrainer 170 according to the first modification example is different from the restrainer 70 according to the abovementioned embodiment in that as illustrated in FIG. 14A, a grid 173 is provided at the opening portion 71 that is configured to expose the intended puncture region S.

The grid 173 is provided so as to cover the opening portion 71. Each space 174 of the grid 173 is formed of a size that allows a medical appliance, such as a sheath, to be inserted via the puncture site into the living body, to be inserted.

The control unit 81 may cause, for example, the camera 41 to detect the grid 173. The control unit 81 may determine, from a correspondence relation between the position of the radial artery V detected by the blood vessel detection unit 30 and the grid 173 detected by the camera 41, the space 174 in which the radial artery V is detected, and control the puncture actuator 61 and the forward mechanism 62 so as to insert the puncture needle N into the determined space 174.

The restrainer 270 according to the second modification example can include, similar to the restrainer 70 according to the abovementioned embodiment, an annular member, a band or band body, or the like that surrounds at least the wrist. The restrainer 270 according to the second modification example is different from the restrainer 70 according to the abovementioned embodiment in the shape of an opening portion 271 configured to expose the intended puncture region S, as illustrated in FIG. 14B.

The opening portion 271 has a circumferential edge portion of a zigzag shape.

The control unit 81 may cause, for example, the camera 41 to detect the circumferential edge portion of the opening portion 271. The control unit 81 may draw a virtual line L that connects facing peak portions 272 or facing valley portions 273 in the circumferential edge portion of the opening portion 271, and form a virtual grid. The control unit 81 may determine, from a correspondence relation between the position of the radial artery V detected by the blood vessel detection unit 30 and the virtual grid, among a plurality of spaces of the grid, a space from which the radial artery V has been detected, and control the operation of the puncture actuator 61 such that the puncture needle N is inserted into the determined space.

(Modification Example of Marker)

Figure 15:
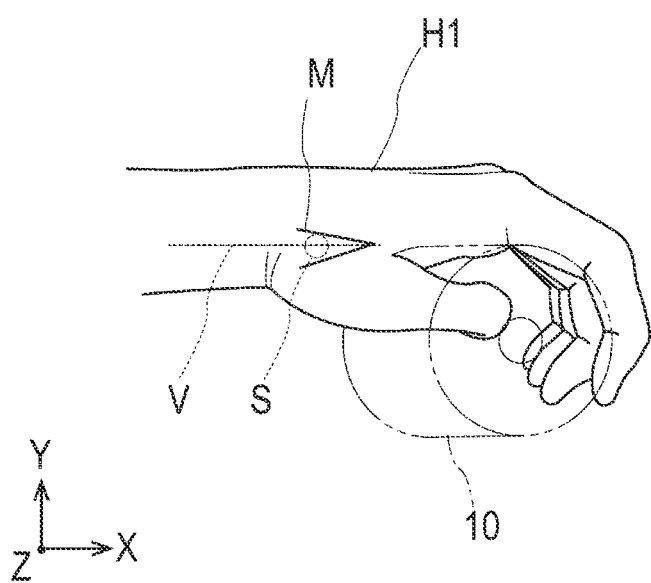
FIG. 15 is a view illustrating a marker according to a modification example.

FIG. 15 illustrates a marker M according to a modification example.

As illustrated in FIG. 15, the marker M indicating the intended puncture region S may be formed by drawing a line that surrounds the intended puncture region S on the hand H1 with a pen or the like. The marker M may be drawn by the multi-degree-of-freedom robot arm or the like included in the puncture system 1, or may be drawn by the operator.

As illustrated in FIG. 15, the marker M may partially surround the intended or planned puncture region S, or may entirely surround the intended or planned puncture region S.

As in the foregoing, the present invention has been explained with the embodiment and the modification examples, however, the present invention is not limited to the respective explained configurations, but can be changed as appropriate within the scope of the invention.

For example, in the abovementioned embodiment, the example in which the puncture system includes the restrainer that suppresses the motion of the wrist has been explained, but the puncture system does not need to include the restrainer. In this case, the puncture system is preferably configured so as to allow, by causing a hand and a wrist of the patient to wear a globe having a motion-capture function, the bends of the joints of the hands and the wrist to be detected.

Moreover, for example, in the abovementioned embodiment, the example in which the adjustment mechanism includes both of the grip actuator and the puncture actuator has been explained, however, the puncture system may only one of the grip actuator and the puncture actuator.

Moreover, for example, in the abovementioned embodiment, the example in which the puncture system detects the marker has been explained, however, the puncture system does not need to detect the marker.

Moreover, for example, in the abovementioned embodiment, as illustrated in FIG. 1, the example in which the grip actuator 20, the detection actuator 50, the puncture actuator 61, and the forward mechanism 62 are disposed to a side of a right hand of the patient has been explained. However, the arrangement of the grip actuator 20, the detection actuator 50, the puncture actuator 61, and the forward mechanism 62 is not specifically limited to the arrangement illustrated in FIG. 1. For example, the detection actuator 50 may be disposed to a side of a left hand of the patient.

The detailed description above describes embodiments of a puncture system and a puncture method representing examples of the inventive puncture system and puncture method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A puncture system configured to automatically puncture a blood vessel of a hand of a patient by a puncture needle, the puncture system comprising:
   a grip to be gripped by the hand of the patient;
   a blood vessel detection unit configured to detect a position of the blood vessel of the hand of the patient that grips the grip;
   an adjustment mechanism configured to adjust a relative posture of the grip and the puncture needle;
   a forward mechanism configured to move the puncture needle forward toward the grip; and
   a control unit that determines, in accordance with the position of the blood vessel detected by the blood vessel detection unit, the relative posture of the grip and the puncture needle and a forward movement distance to move the puncture needle, and controls operations of the adjustment mechanism and the forward mechanism based on the posture of the grip and the forward movement distance determined by the control unit.

2. The puncture system according to claim 1, wherein the adjustment mechanism includes a grip actuator connected to the grip and configured to adjust a posture of the grip.

3. The puncture system according to claim 1, wherein the adjustment mechanism includes a puncture actuator configured to adjust a posture of the puncture needle.

4. The puncture system according to claim 3, wherein the blood vessel detection unit simultaneously detects the position of the blood vessel and the position of the puncture needle, and
   the puncture actuator adjusts the posture of the puncture needle in accordance with the position of the blood vessel and the position of the puncture needle detected by the blood vessel detection unit.

5. The puncture system according to claim 1, wherein the adjustment mechanism includes a grip actuator configured to adjust a position and a posture of the grip, and a puncture actuator configured to adjust a position and a posture of the puncture needle, and
   the control unit acquires data on the position and the posture of the grip, and also acquires data on the position and the posture of the puncture needle.

6. The puncture system according to claim 1, further comprising a reversed blood detection unit configured to detect reversed blood flow into the puncture needle.

7. The puncture system according to claim 1, further comprising a marker detection unit configured to detect a position of a marker indicating an intended puncture region of the hand,
the blood vessel detection unit being configured to detect the blood vessel in the intended puncture region.

8. The puncture system according to claim 1, further comprising a detection actuator configured to adjust a position and a posture of the blood vessel detection unit.

9. The puncture system according to claim 1, wherein the grip includes a hole portion into which a thumb of the hand is insertable, and
further comprising a thumb detection unit that detects contact of the thumb with the thumb detection unit, the thumb detection unit being positioned in the hole portion.

10. The puncture system according to claim 1, further comprising a restrainer configured to be worn on a wrist of the patent to suppress motion of the wrist.

11. A puncture system configured to automatically puncture a blood vessel in a hand of a patient with a puncture needle, the patient's hand including fingers and a thumb, the puncture system comprising:
a grip to be gripped by the hand of the patient, the grip including a hole sized to receive the thumb of the patient's hand or at least one of the fingers of the patent's hand;
a grip actuator that holds the grip and adjusts a posture of the grip;
a puncture needle holder configured to hold the puncture needle and move the puncture needle toward and away from the grip;
a puncture needle actuator operatively connected to the puncture needle holder to adjust a posture of the puncture needle;
a blood vessel detection unit that detects a position of the blood vessel of the hand of the patient that grips the grip; and
a control unit that determines, in accordance with the position of the blood vessel detected by the blood vessel detection unit and a relative posture of the grip and the puncture needle, a forward movement distance to move the puncture needle to puncture the blood vessel in the hand of the patient, and controls operations of the puncture needle holder based on the forward movement distance determined by the control unit.

12. The puncture system according to claim 11, wherein the grip actuator comprises a multi-degree-of-freedom robot arm.

13. The puncture system according to claim 11, wherein the puncture needle holder comprises a multi-degree-of-freedom robot arm.

14. The puncture system according to claim 11, further comprising a reversed blood detection unit configured to detecting blood flowing into the puncture needle when the blood vessel has been punctured by the puncture needle.

15. The puncture system according to claim 11, further comprising a detection unit that detects contact of the thumb or the one of the fingers with the detection unit, the detection unit being positioned in the hole portion in the grip.

16. A method of automatically puncturing a blood vessel in a hand of a patient with a puncture needle, the method comprising:
detecting a position of a blood vessel in a hand of a patient while the hand of the patient is gripping a grip;
determining a relative posture of the grip and the puncture needle, and a forward movement distance to move the puncture needle, using the detected position of the blood vessel;
changing the posture of the grip and/or the puncture needle so that the relative posture of the grip and the puncture needle is the determined relative posture of the grip and the puncture needle; and
moving the puncture needle the forward movement distance to puncture the blood vessel.

17. The method according to claim 16, wherein the gripping of the grip includes positioning a thumb of the patient's hand or at least one finger of the patent's hand in a hole in the grip.

18. The method according to claim 17, wherein the determining of the relative posture of the grip is performed only if a detection unit positioned in the hole of the grip detects the thumb of the patient's hand or the at least one finger of the patient's hand.

19. The method according to claim 16, further comprising, after moving the puncture needle the forward movement distance, detecting whether blood is flowing into the puncture needle, and moving the puncture needle away from the patient's hand when blood is not detected as flowing into the puncture needle.

* * * * *